(12) United States Patent
Sweeney et al.

(10) Patent No.: US 9,636,292 B2
(45) Date of Patent: *May 2, 2017

(54) TOPICAL SKIN CARE COMPOSITION FOR NIGHT USE

(71) Applicant: Truth Aesthetics LLC, Austin, TX (US)

(72) Inventors: Sara Sweeney, Austin, TX (US); Fred H. Khoury, Chatsworth, CA (US)

(73) Assignee: Truth Aesthetics LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/814,017

(22) Filed: Jul. 30, 2015

(65) Prior Publication Data

US 2017/0027838 A1    Feb. 2, 2017

(51) Int. Cl.

| | | |
|---|---|---|
| *A61K 8/97* | (2017.01) | |
| *A61K 8/73* | (2006.01) | |
| *A61Q 19/08* | (2006.01) | |
| *A61K 8/66* | (2006.01) | |
| *A61K 8/44* | (2006.01) | |
| *A61K 8/64* | (2006.01) | |
| *A61K 8/67* | (2006.01) | |

(52) U.S. Cl.
CPC ............... *A61K 8/66* (2013.01); *A61K 8/445* (2013.01); *A61K 8/64* (2013.01); *A61K 8/676* (2013.01); *A61K 8/73* (2013.01); *A61K 8/97* (2013.01); *A61Q 19/08* (2013.01)

(58) Field of Classification Search
None
See application file for complete search history.

(56) References Cited

U.S. PATENT DOCUMENTS

| | | |
|---|---|---|
| 6,071,541 A | 6/2000 | Murad |
| 6,338,855 B1 | 1/2002 | Albacarys et al. |
| 6,375,992 B1 | 4/2002 | Blumenstein-Stahl et al. |
| 6,630,163 B1 | 10/2003 | Murad |
| 7,320,797 B2 | 1/2008 | Gupta |
| 8,071,555 B2 | 12/2011 | Zhang et al. |
| 8,211,873 B2 | 7/2012 | Gupta et al. |
| 8,586,730 B2 | 11/2013 | Peter et al. |
| 2008/0107679 A1 | 5/2008 | Dilallo et al. |
| 2010/0047193 A1 | 2/2010 | Fishman |
| 2011/0229538 A1 | 9/2011 | Matravers et al. |
| 2013/0028853 A1 | 1/2013 | Nurse et al. |
| 2013/0039961 A1 | 2/2013 | Gonzales et al. |
| 2013/0172291 A1 | 7/2013 | Peter et al. |
| 2013/0336903 A1 | 12/2013 | Fernandez Prieto et al. |
| 2013/0336909 A1 | 12/2013 | Garaud et al. |

OTHER PUBLICATIONS

International Search Report for PCT/US16/41140 dated Aug. 5, 2016.

*Primary Examiner* — Suzanne M Noakes
*Assistant Examiner* — Stephen Chong
(74) *Attorney, Agent, or Firm* — Rutan & Tucker LLP; Hani Z. Sayed

(57) ABSTRACT

Topical skin care composition for night use containing a combination of stabilized anti-oxidants, oat derived avenanthramides, retinol-like compounds and biofunctional peptides and other optional ingredients for topical application for the treatment and prevention of skin damage due to environmental factors.

20 Claims, No Drawings

TOPICAL SKIN CARE COMPOSITION FOR NIGHT USE

BACKGROUND

This invention is related to a topical skin care composition as well as methods of using same. More specifically, the invention relates to a topical skin care composition for use during the night to rejuvenate the skin and reverse the signs of aging.

The skin ages as a natural consequence of exposure to various environmental factors. Among these factors is exposure to air pollutants, as well as thermal and infra-red radiation. It is reported that over 85% of the visible signs of aging are due to the negative effect of these factors on the skin. Other factors that may play a part in the aging process of the skin include, for example, weathering of the skin, exposure to cigarette smoke and Ultra-Violet (UV) radiation.

Most conventional cosmetic products merely temporarily mask the signs of aging, and do little to adequately protect the skin's collagen and elastin network from the effects of the environmental factors listed above. What has been needed, and heretofore unavailable, is a topically applied skin care formulation for use in the evening that assists in rejuvenating the skin and reversing the signs of aging caused by exposure to environmental factors during the day. The present invention satisfies these and other needs.

SUMMARY OF THE INVENTION

In its most general aspect, the invention includes a topical skin care composition containing a combination of compounds having a retinol-like activity, including a peptide with retinol-like activity; an oat avenanthramide extract; capryloyl pentapeptide-26; a soy based complex; an argfrilene-like peptide; a hydrating complex of marine-based, high water binding constituents; a mushroom derived, water soluble enzyme; an aloe leaf extract; an oat β-glucan, such as colloidal oatmeal; allantoin; an extract from dried apples; an all-natural anti-oxidant complex composed of rice extract, rosemary extract, sunflower extract and natural tocopherols; a stable, oil soluble form of Vitamin C (ascorbic acid); and daikon radish oil. The combination promotes rejuvenation of the skin and inhabits damage to skin caused by dehydration and environmental factors. As a result, the composition provides surprising performance benefits in reducing or removing fine lines and wrinkles, firming the skin, hydrating the skin and promoting a younger appearance.

In another aspect, the various components described above are blended with a cosmetically acceptable carrier which may include purified water, oils, alcohols, glycols, and combinations thereof.

In yet another aspect, the topical skin care composition may further comprise additional ingredients such as penetration enhancers, humectants, lubricants, pharmaceutically active agents, color, fragrance, preservatives, antioxidants, chelators, neutralizers, amino acids, anti-inflammatory agents, anti-irritants, anti-tack agents, astringents, binders, catalysts, stabilizers, emollients, emulsifiers, surfactants, cell-signaling agents, essential oils, plant/botanical extracts, conditioners, film formers, gelling agents, foaming agents, exfoliants, vitamins, minerals, pH adjusters, proteins, peptides, tactile enhancers, saccharides, solvents or any combination thereof.

In still another aspect, the topical skin care composition may be formulated as a cream, lotion, serum, facial cleanser, toner, eye cream, sunscreen, stick, spray, impregnated personal care device, impregnated towelette, gel, fluid/liquid, soap, oil, butter, peel, scrub, mask, concentrate, or any other form known in the art.

In another aspect, the present invention includes a topical skin care composition comprising: (a) a meroterpene; (b) a source of bio-retinol (c) a source of retinol-like activity; (d) an oat avenanthramide extract; (e) an anti-inflammatory peptide; (f) a soy based active complex; (g) an argirilene-like peptide; (h) a source of sodium hyaluronic acid; (j) a water soluble enzyme; (k) an aloe barbadensis leaf extract; (l) a source of oat β-glucan; (m) a source of allantoin; (n) a source of moisturizing saccharide complex; (o) a complex including rice extract, rosemary extract, sunflower extract and tocopherol; (p) an ascorbic acid source; (q) a source of anti-oxidant components; and (r) a cosmetically acceptable carrier.

In a further aspect, the invention includes a method of treating skin comprising applying a topical skin care composition comprising a combination of compounds having a retinol-like activity, including a peptide with retinol-like activity; an oat avenanthramide extract; capryloyl pentapeptide-26; a soy based complex; an argirilene-like peptide; a hydrating complex of marine-based, high water binding constituents; a mushroom derived, water soluble enzyme; an aloe leaf extract; an oat β-glucan, such as colloidal oatmeal; allantoin; an extract from dried apples; an all-natural anti-oxidant complex composed of rice extract, rosemary extract, sunflower extract and natural tocopherols; a stable, oil soluble form of Vitamin C; and daikon radish oil, and a cosmetically acceptable carrier.

In one aspect, the aloe barbadensis extract is present in the amount of 0.01% to 0.50% by weight. In another aspect, the source of ascorbic acid is tetrahexydecyl ascorbate. In yet another aspect, the source of ascorbic acid is present in the amount of 0.01% to 10% by weight.

In still another aspect, the meteropene is bakuchiol. In yet another aspect, The topical skin care composition of claim 1, wherein the source of anti-oxidant components is daikon radish oil. In yet another aspect, the source of moisturizing saccharide complex is an apple extract. In another aspect, the water soluble enzyme is derived from mushroom.

In yet another aspect, the source of oat β-glucan is colloidal oatmeal. In still another aspect, the argirilene-like peptide is palmitoyl hexapeptide-19. In another aspect, the source of sodium hyaluronic acid further includes *chondrus crispus* extract and hydrolyzed *chrondrus crispus* extract.

In one further aspect, the topical skin care composition of the invention includes one or more emollient compounds. In another further aspect, the topical skin care composition of the invention includes an emulsifier. In one further aspect, the topical skin care composition of the invention includes a pH modifier. In yet another further aspect, the topical skin care composition of the invention includes a viscosity modifier.

In still another aspect, the anti-inflammatory peptide is capryloyl pentapeptide-26. In yet another aspect the source of retinol-like activity is myristoyl tripeptide-31. In yet another aspect, the water soluble enzyme is a mucor miehei extract.

In another aspect, the source of bio-retinol is a complex of bidens pilosa extract, elaeis guineesis oil, gossypium herbaceum seed oil, and linum usitatissimum seed oil.

In still another aspect, the present invention includes a method of treating the skin comprising applying to an outer surface of the skin a topical skin care composition comprising a meroterpene; a source of bio-retinol; a source of retinol-like activity; (d) an oat avenanthramide extract; an anti-inflammatory peptide; a soy based active complex; (g) an argirilene-like peptide; (h) a source of sodium hyaluronic acid; a water soluble enzyme; an aloe barbadensis leaf extract; a source of oat β-glucan; a source of allantoin; a source of moisturizing saccharide complex; a complex including rice extract, rosemary extract, sunflower extract and tocopherol; an ascorbic acid source; a source of anti-oxidant components; and a cosmetically acceptable carrier.

In still another aspect, a topical skin care composition in accordance with principles of the invention is applied to the skin, often the face, which may, for example, but not limited to, have wrinkles, fine lines, uneven tone, loss of firmness, surface roughness, dark circles, under-eye puffiness, sun damage, redness, dryness, irritation, enlarged ports and combinations of all or some of the above. Alternatively, the topical skin care composition may be applied to the skin to prevent the occurrence of the various problems described above.

In yet another aspect, a topical skin care composition in accordance with principles of the invention is applied to skin in an amount and for a period of time sufficient to treat the skin for the condition treated. In one alternative aspect, the topical skin care composition is applied at least once a day. In another alternative aspect, the topical skin care composition is applied more than once a day.

In still another aspect, a user of a topical skin care composition in accordance with principles of the invention cleanses his/her skin and gently pats the skin dry. A thin, even layer of the topical skin care composition of the present invention is applied to the face, neck, or other portions of the body. The topical skin care composition is then gently massaged into the skin. This process may be performed every evening, for example.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

As used herein, the phrases "selected from the group consisting of," "chosen from," and the like include mixtures of the specified materials. Terms such as "contains" and the like are meant to include "including at least" unless otherwise specifically noted.

Where a numerical limit or range is stated, the endpoints are included. Also, all values and subranges within a numerical limit or range are specifically included as if explicitly written out.

The various embodiments and compositions described herein are typically used by persons desiring to protect their skin from harmful environmental factors, or to repair skin that has been previously damaged by such factors. For example, persons using those compositions may seek to prevent damage to the skin caused by lack of hydration, inflammation or infrared radiation. Benefits of using the compositions of the present invention include retaining and/or restoring and/or improving physical and mechanical properties of the skin which includes smoothness, taughtness, resiliency and radiance.

The present invention is directed to a topical skin care composition containing a combination of compounds having a retinol-like activity, including a peptide with retinol-like activity; an oat avenanthramide extract; capryloyl pentapeptide-26; a soy based complex; an argirilene-like peptide; a hydrating complex of marine-based, high water binding constituents; a mushroom derived, water soluble enzyme; an aloe leaf extract; an oat β-glucan, such as colloidal oatmeal; allantoin; an extract from dried apples; an all-natural anti-oxidant complex composed of rice extract, rosemary extract, sunflower extract and natural tocopherols; a stable, oil soluble form of Vitamin C (ascorbic acid); daikon radish oil; and various other components forming an acceptable cosmetic carrier, pH adjusters, thickeners, and the like known to those skilled in the art. The combination promotes rejuvenation of the skin and inhabits damage to skin caused by dehydration and environmental factors. As a result, the composition provides surprising performance benefits in reducing or removing fine lines and wrinkles, firming the skin, hydrating the skin and promoting a younger appearance.

One of the retinol-like compounds is bakuchiol, a meroterpene. The bakuchiol used in the compositions of the present invention may be obtained from commercial sources. Bakuchiol has been found to have retinol-like activity without the negative side-effects of retinol. Bakuchiol functions as a skin protectant, has a high anti-oxidant profile, and has been found to have a strong inhibitory effect against UV induced erythema as well as having broad-spectrum anti-bacterial and anti-fungal activities, including anti-acne activity. One source for bakuchiol is Sytenol®A sold by Sytheon Ltd.

According to one embodiment or composition of the invention, the bakuchiol is present in an amount ranging from 0.1% to 3.0% by weight of the topical skin care composition, and preferably from about 0.9% to 2.0% by weight of the topical skin care composition, and most preferably in an amount ranging from 1.0% to 1.19% by weight of the topical skin care composition.

Another retinol-like compound used in the compositions of the present invention is a bio-retinol having retinoid receptor activity that mimics the results of retinoids to fight skin aging, and may be obtained from commercial sources. This compound may include *bidens pilosa* extract, *elaeis guineensis* (palm) oil, *gossypium herbaceum* (cotton) seed oil, and *linum usitatissimum* (linseed) seed oil, and natural tocopherol. Compounds of this type have been found to reduce the appearance of wrinkles, improve skin elasticity, and result in younger looking, luminous and firm skin. Such compounds also display anti-inflammatory and anti-oxidant activity. One source for such a compound is Revinage, sold by Chemyunion Quimica Ltd (Brazil).

According to one embodiment or composition of the invention, the bio-retinol compound described above is present in an amount ranging from 0.10% to 3.0% by weight of the topical skin care composition, and preferably from about 1.0% to 2.2% by weight of the topical skin care composition, and most preferably in an amount ranging from 1.8% to 2.0% by weight of the topical skin care composition.

The peptide with retinol-like activity used in the compositions of the present invention may be obtained from commercial sources. The peptide with retinol-like activity has been found to increase collagen synthesis and provide an anti-aging effect against damage to the skin caused by UV irradiation. One source for such a peptide is DennaPep™ A350 sold by Miwon Commercial Co., Ltd, which includes myristoyl tripeptide-31 and butylene glycol.

According to one embodiment or composition of the invention, the peptide with retinol-like activity is present in an amount ranging from 0.1% to 4.0% by weight of the topical skin care composition, and preferably from about 1.0% to 2.2% by weight of the topical skin care composition, and most preferably in an amount ranging from 1.8% to 2.0 by weight of the topical skin care composition.

The oat avenanthramide extract used in the compositions of the present invention may be obtained from commercial sources. The oat avenanthramide extract has been found to be a natural anti-oxidant and anti-irritant that protects from UV exposure and reduces redness, inflammation and itching of the skin. One source for such an oat avenanthramide extract is CP Oat Avenanthramide Extract 902-3043 sold by Ceapro, Inc., which includes avena sativa (oat) extract, water, glycerin and potassium sorbate.

According to one embodiment or composition of the invention, the oat avenanthramide extract is present in an amount ranging from 0.1% to 3.0% by weight of the topical skin care composition, and preferably from about 0.3% to 2.0% by weight of the topical skin care composition, and most preferably in an amount ranging from 0.9% to 1.1% by weight of the topical skin care composition.

The capryloyl pentapeptide-26 used in the compositions of the present invention is a multifunctional anti-inflammatory peptide useful for repairing irritated and sensitive skin, and may be obtained from commercial sources. The capryloyl pentapeptide-26 has been found to reduce itching and pruritus caused by environmental causes, such as UV irradiation. One source for capryloyl pentapeptide-26 is DermaPep™ A530 sold by Miwon Commercial Co., Ltd., which includes capryloyl pentapeptice-26, glycerin, and butylene glycol.

According to one embodiment or composition of the invention, the capryloyl pentapeptide-26 is present in an amount ranging from 0.1% to 4.0$ by weight of the topical skin care composition, and preferably from about 1.0% to 2.2% by weight of the topical skin care composition, and most preferably in an amount ranging from 1.8% to 2.0% by weight of the topical skin care composition.

The soy based complex used in the compositions of the present invention may be obtained from commercial sources. The soy based complex has been found to improve hydration, clarity, and firmness of the skin. The soy based complex has also been found to provide anti-flakiness and anti-wrinkle benefits. One source for such a soy based complex is Allosteris, which includes water, glycerin, glycine (soybean) soja extract, and Phenoxethanol, sold by Barnet Products Corporation.

According to one embodiment or composition of the invention, the soy based complex is present in an amount ranging from 0.1% to 3.0% by weight of the topical skin care composition, and preferably from about 0.9% to 2.0% by weight of the topical skin care composition, and most preferably in an amount ranging from 1.0% to 1.1% by weight of the topical skin care composition.

The argirilene-like peptide used in the compositions of the present invention is a Botox®-like neural inhibitor that has been shown to markedly reduce the appearance of wrinkles, and may be obtained from commercial sources. One source for such an argirilene-like peptide is Botaniceutical NI-Peptide, containing water and palmitoyl hexapeptide-19, sold by Botanigenics, Inc.

According to one embodiment or composition of the invention, the argirilene-like peptide is present in an amount ranging from 0.1% to 5.5% by weight of the topical skin care composition, and preferably from about 3.0% to 5.0% by weight of the topical skin care composition, and most preferably in an amount ranging from 4.05% to 5.0% by weight of the topical skin care composition.

The hydrating complex of marine-based, high water binding constituents used in the compositions of the present invention may be obtained from commercial sources. The hydrating complex of marine-based, high water binding constituents has been found to help maintain the moisture balance of the skin, which helps keep the skin hydrated and supple. One source for such a hydrating complex of marine-based, high water binding constituents is Marimoist, which contains water, *chondrus crispus* extract, hydrolyzed *chondrus crispus* extract, sodium hyaluronate, pheoxyethanol, potassium sorbate, butylene glycol, sodium dihydroacetate, and citric acid, sold by BioCogent LLC.

According to one embodiment or composition of the invention, the hydrating complex of marine-based, high water binding constituents is present in an amount ranging from 0.5% to 10% by weight of the topical skin care composition, and preferably from about 1.0% to 5.0% by weight of the topical skin care composition, and most preferably in an amount ranging from 2.7% to 3.3% by weight of the topical skin care composition.

The mushroom derived, water soluble enzyme used in the compositions of the present invention may be obtained from commercial sources. The mushroom derived, water soluble enzyme has been found to exfoliate the skin without compromising the skin's barrier function or reactivity. It has also been found to increase skin cell renewal, and deliver long term rejuvenating benefits such as improving skin firmness, increasing skin clarity, reducing wrinkles and increasing skin moisture. One source for such a mushroom derived, water soluble enzyme is Actizyme® E3M-M sold by Active Organics, which includes mucor miehei extract, butylene glycol, and water.

According to one embodiment or composition of the invention, the mushroom derived, water soluble enzyme is present in an amount ranging from 0.5% to 10.0% by weight of the topical skin care composition, and preferably from about 1.0% to 5.0% by weight of the topical skin care composition, and most preferably in an amount ranging from 2.25% to 2.75% by weight of the topical skin care composition.

The aloe leaf extract used in the compositions of the present invention may be obtained from commercial sources or harvested according to known collection and extraction procedures. The aloe leaf extract may be an extract of the leaves of aloe barbadensis. This extract provides a combination of vitamins, minerals and amino acids that has been found to hydrate and soothe skin irritations. One source for such an extract is Aloe Barbadensis Leaf Extract 200× sold by Concentrated Aloe Corporation (Ormond Beach, Fla.)

According to one embodiment or composition of the invention, the aloe barbadensis extract is present in an amount ranging from 0.01% to 0.5% by weight of the topical skin care composition, and preferably from about 0.05% to 0.11% by weight of the topical skin care composition, and most preferably in an amount ranging from 0.09% to 0.10% by weight of the topical skin care composition.

The oat β-glucan (colloidal oatmeal) used in the compositions of the present invention may be obtained from commercial sources. The oat β-glucan has been found to penetrate and moisturize the skin, and to promote procollagen formation, One source for such a oat β-glucan is Colloidal Oatmeal Irradiated sold by Oat Cosmetics or Charkit Chemical Corporation, which includes avena sativa (oat) kernel flour.

According to one embodiment or composition of the invention, the oat β-glucan is present in an amount ranging from 0.05% to 2.0% by weight of the topical skin care composition, and preferably from about 0.1% to 2.0% by weight of the topical skin care composition, and most preferably in an amount ranging from 0.225% to 0.275% by weight of the topical skin care composition.

The allantoin used in the compositions of the present invention may be obtained from commercial sources. The allantoin has been found to increase the capacity of corneocytes to bind water and reinforce the skin's natural protective barrier. Allantoin also improves moisture retention by the skin, helping to smooth the skin. Allantoin is an anti-irritant, and also exfoliates dry and damaged cells, and has been found to boost the radiant appearance of the skin. Allantoin is available from various supply houses.

According to one embodiment or composition of the invention, the allantoin is present in an amount ranging from 0.05% to 2.0% by weight of the topical skin care composition, and preferably from about 0.09% to 0.2% by weight of the topical skin care composition.

The extract from dried apples used in the compositions of the present invention may be obtained from commercial sources. The extract from dried apples is a moisturizing saccharide complex that has been found to moisturize and smooth skin texture. One source for such an extract from dried apples is Botanimoist AMS, which contains *Pyrus Malus* (Apple) extract and glycerin, sold by Botanigenics, Inc.

According to one embodiment or composition of the invention, the extract from dried apples is present in an amount ranging from 0.5% to 10.0% by weight of the topical skin care composition, and preferably from about 2.0% to 5.0% by weight of the topical skin care composition, and most preferably in an amount ranging from 2.7% to 3.3% by weight of the topical skin care composition.

The natural anti-oxidant complex composed of rice extract, rosemary extract, sunflower extract and natural tocopherols used in the compositions of the present invention may be obtained from commercial sources. This complex has been found to protect natural oils of the skin from oxidative degradation. One source for such an anti-oxidant complex is Bottanessential RRST sold by Botanigenics (USA), which includes *oryza sativa* (rice) bran extract, *rosmarinus officinalis* (rosemary) leaf extract, *heliantus annuus* (sunflower) seed oil, and tocopherol.

According to one embodiment or composition of the invention, the anti-oxidant complex is present in an amount ranging from 0.1% to 2.0% by weight of the topical skin care composition, and preferably from about 0.1% to 1.1% by weight of the topical skin care composition, and most preferably in an amount ranging from 0.9% to 1.0% by weight of the topical skin care composition.

The stable, oil based source of Vitamin C (ascorbic acid) used in the compositions of the present invention may be obtained from commercial sources. The stable, oil based source of Vitamin C has been found to provide anti-oxidant protection along with promotion of collagen synthesis to normalize uneven skin tone an diminish age spots. One source for such a stable, oil based source of Vitamin C is BV-OSC, sold by Barnett Products Corporation (Edgewood Cliffs, N.J.)

According to one embodiment or composition of the invention, the stable, oil based source of Vitamin C is present in an amount ranging from 0.1% to 10.0% by weight of the topical skin care composition, and preferably from about 0.095% to 3.0% by weight of the topical skin care composition, and most preferably in an amount ranging from 0.1% to 0.11% by weight of the topical skin care composition.

The Daikon radish oil (*raphanus sativus* (radish) seed oil) used in the compositions of the present invention may be obtained from commercial sources. Daikon radish oil has been found to have high antioxidant levels, and provides lightweight emoliency and natural moisturization. One source for such Daikon radish oil is Daikon Radish Oil 1304071450, sold by Charket.

According to one embodiment or composition of the invention, the Daikon radish oil is present in an amount ranging from 0.1% to 10.0% by weight of the topical skin care composition, and preferably from about 0.9% to 5.0% by weight of the topical skin care composition, and most preferably in an amount ranging from 1.0% to 1.5% by weight of the topical skin care composition.

Other components may also be included in the compositions of various embodiments of the present invention. For example, ammonium acryloyldimethlytaurate/VP copolymer, sold by Clariant, may be used as an emulsifying agent; Xanthan gum, such as Keirol CG-RD, sold by CP Keico, may be used to adjust viscosity; trisodium ethylenediamine disuccinate, such Natriquest E30, sold by Innospec, may used as a chelating agent; a compound such as PolyAquaol-2W, sold by Innovacos, and containing polyglycerl-2 stearate, glyceryl stearate, and stearyl alcohol, may be used as an emulsifier; caprylic/capric triglyceride, available from local sources, and caprylyl-caprylate/caprate, available from BASF, may be used as emollients; a mixture of propanediol, ethylhexylgycerin, and potassium sorbate, such as Linatural MBS-1, sold by Lincoln Fine Ingredients, may be used as a preservative; and citric acid may be used to adjust the pH of the compound.

The invention is now more fully illustrated using the following example, which is not to be understood as limiting the invention to the embodiments described.

Example 1

A topical cream for day use was prepared using the ingredients set forth in Table 1 below.

TABLE 1

| | Ingredient | % w/w |
|---|---|---|
| | PHASE A | |
| 1 | Water (USP) | 66.575 |
| 2 | Ammonium Acryloyldimethyltaurate/VP Copolymer | 0.650 |
| 3 | Xanthan Gum | 0.125 |
| 4 | *Aloe Barbadensis* Leaf Extract | 0.100 |
| 5 | *Avena Sative* (Oat) Kernel Flour | 0.250 |
| 6 | Trisodium Ethylenediamine Disuccinate | 0.100 |
| 7 | Allantoin | 0.100 |
| 8 | *Pyrus Malus* (Apple) Fruit Extract Glycerin | 3.000 |
| 9 | Water *Chondrus Crispus* Extract Hydrolyzed *Chondrus Crispus* Extract Sodium Hyaluronate Phenoxyethanol Potassium Sorbate Butylene Glycol Sodium Dihdroacetate | 3.000 |

TABLE 1-continued

| | Ingredient | % w/w |
|---|---|---|
| | Citric Acid | |
| | PHASE B | |
| 10 | Polygyceryl-2-Stearate<br>Glyceryl Stearate<br>Stearyl Alcohol | 1.250 |
| 11 | Caprylic/Capric Triglyceride | 1.000 |
| 12 | Caprylyl-Caprylate/Caprate | 3.000 |
| 13 | *Raphanus Sativus* (Radish) Seed Oil | 1.000 |
| 14 | *Bidens Pilosa* Extract<br>*Elaeis Guinessis* (Palm) Oil<br>*Gossypium Herbaceum* (Collton) Seed Oil<br>*Linum Usitatissimum* (Linseed) Seed Oil | 2.000 |
| 15 | *Oryza Sativa* (Rice) Bran Extract<br>*Rosamrinums Officinalis* (Rosemary) Leaf Extract<br>*Heliantus Annuus* (Sunflower) Seed Oil<br>Tocopherol | 1.000 |
| | PHASE C | |
| 16 | Tetrahexydecyl Ascorbate | 0.100 |
| 17 | Bakuchiol | 1.000 |
| 18 | Citric Acid | 0.250 |
| 19 | Mucor Miehei Extract<br>Butylene Glycol<br>Water | 2.500 |
| 20 | Propanediol<br>Ethylhexyglycerin<br>Potassium Sorbate | 2.000 |
| 21 | Water<br>Glycerin<br>*Glycine* (Soybean) *Soja* Extract<br>Phenoxethanol | 1.000 |
| 22 | *Avena Sativa* (Oat) Extract<br>Water<br>Glycerin<br>Potassium Sorbate | 1.000 |
| 23 | Water<br>Palmitoyl Hexapeptide-19 | 5.000 |
| 24 | Myristoyl Tripeptide-31<br>Butylene Glycol | 2.000 |
| 25 | Capryloyl Pentapeptide-26<br>Glycerin<br>Butylene Glycol | 2.000 |

The night cream was prepared by combining the ingredients of Phase A and Phase B in separate mixing tanks and heating the tanks to 80 degrees centigrade. Phase B was then added to Phase A, and the mixture was homogenized for five minutes and then cooled to 45 degrees centigrade. Phase C was then added to the homogenized mixture of Phase A and Phase B, and mixed until a uniform consistence was obtained. The mixture was then cooled to 30 degrees centigrade until a homogenous cream suitable for application to the skin of a user was obtained. Mixing was conducted at 30-50 hertz with propeller and side sweep agitation. After 1 hour of missing, a top and bottom sample was evaluated for uniform polymer dispersion.

The resulting topical night cream was an opaque, viscous emulsion, off whicte in color. The pH at 25 degrees centigrade was 3.70-4.20, the viscosity was between 4500-8000 cPs and the specific gravity at 25 degrees centigrade was 0.973-1.013.

Example 2

A topical cream for night use was prepared using the ingredients set forth in Table 2 below.

TABLE 2

| | Ingredient | % w/w |
|---|---|---|
| | PHASE A | |
| 1 | Water (USP) | 68.965 |
| 2 | Ammonium Acryloyldimethyltaurate/VP Copolymer | 1.50 |
| 3 | Xanthan Gum | 0.175 |
| 4 | *Aloe Barbadensis* Leaf Extract | 0.100 |
| 5 | *Avena Sative* (Oat) Kernel Flour | 0.250 |
| 6 | Trisodium Ethylenediamine Disuccinate | 0.100 |
| 7 | Allantoin | 0.200 |
| 8 | *Pyrus Malus* (Apple) Fruit Extract<br>Glycerin | 2.000 |
| 9 | Water<br>*Chondrus Crispus* Extract<br>Hydrolyzed *Chondrus Crispus* Extract<br>Sodium Hyaluronate<br>Phenoxyethanol<br>Potassium Sorbate<br>Butylene Glycol<br>Sodium Dihdroacetate<br>Citric Acid | 2.750 |
| | PHASE B | |
| 10 | Polygyceryl-2-Stearate<br>Glyceryl Stearate<br>Stearyl Alcohol | 1.750 |
| 11 | Caprylic/Capric Triglyceride | 2.000 |
| 12 | Caprylyl-Caprylate/Caprate | 2.000 |
| 13 | *Raphanus Sativus* (Radish) Seed Oil | 1.500 |
| 14 | *Bidens Pilosa* Extract<br>*Elaeis Guinessis* (Palm) Oil<br>*Gossypium Herbaceum* (Collton) Seed Oil<br>*Linum Usitatissimum* (Linseed) Seed Oil | 2.000 |
| 15 | *Oryza Sativa* (Rice) Bran Extract<br>*Rosamrinums Officinalis* (Rosemary) Leaf Extract<br>*Heliantus Annuus* (Sunflower) Seed Oil<br>Tocopherol | 1.000 |
| | PHASE C | |
| 16 | Tetrahexydecyl Ascorbate | 0.100 |
| 17 | Bakuchiol | 1.000 |
| 18 | Citric Acid | 0.220 |
| 19 | Mucor Miehei Extract<br>Butylene Glycol<br>Water | 1.000 |
| 20 | Propanediol<br>Ethylhexyglycerin<br>Potassium Sorbate | 2.000 |
| 21 | Water<br>Glycerin<br>*Glycine* (Soybean) *Soja* Extract<br>Phenoxethanol | 1.000 |
| 22 | *Avena Sativa* (Oat) Extract<br>Water<br>Glycerin<br>Potassium Sorbate | 1.000 |
| 23 | Water<br>Palmitoyl Hexapeptide-19 | 3.000 |
| 24 | Myristoyl Tripeptide-31<br>Butylene Glycol | 2.000 |
| 25 | Capryloyl Pentapeptide-26<br>Glycerin<br>Butylene Glycol | 2.000 |
| 26 | Citric Acid | 0.390 |

The night cream was prepared by combining the ingredients of Phase A and Phase B in separate mixing tanks and heating the tanks to 80 degrees centigrade. Phase B was then added to Phase A, and the mixture was homogenized for five minutes and then cooled to 45 degrees centigrade. Phase C was then added to the homogenized mixture of Phase A and Phase B, and mixed until a uniform consistence was obtained. The mixture was then cooled to 30 degrees centigrade until a homogenous cream suitable for application to the skin of a user is obtained. Mixing was conducted at 30-50 hertz with propeller and side sweep agitation. After 1 hour of mixing, a top and bottom sample was evaluated for uniform polymer dispersion.

The resulting topical night cream was an opaque, viscous emulsion, off white in color. The pH at 25 degrees centigrade was 3.70-4.20, the viscosity was between 4500-8000 cPs and the specific gravity at 25 degrees centigrade was 0.973-1.013.

The examples presented above provide a process for making and using the various embodiments of the invention to enable a person skilled in the art to make and use the same. It will be understood that the various examples may be used to protect a user's face and other skin areas from the harmful effects of various environmental factors. It will also be understood that the various embodiments of the invention may be used in concert with other topical liquids, creams, sprays and the like without departing from the intended scope of the invention.

In another embodiment, the invention includes a method of treating skin comprising applying the topical skin care composition such as is described above to the skin. Typically, the topical skin care composition is applied to the skin, often the face, which may, for example, but not limited to, have wrinkles, fine lines, uneven tone, loss of firmness, surface roughness, dark circles, under-eye puffiness, sun damage, redness, dryness, irritation, enlarged ports and combinations of all or some of the above. Alternatively, the topical skin care composition may be applied to the skin to prevent the occurrence of the various problems described above.

The novel compositions of the present invention are used by subjects desiring to obtain the benefits noted above, including the hydration of their skin, increasing the skins resiliency and radiance, and providing protection against inflammation-related signs of aging, such as fine lines and wrinkles. Use of the various compositions of the invention may decrease the size of skin pores, even out the tone of the skin, and improve the texture of the skin.

Typically, a person using the compositions of the invention apply them to the their skin in amounts that obtain one or more of the noted benefits. For example, the compositions of the invention may be applied to a skin area so as to improve the texture of the skin, reduce pore size, or hydrate dry skin. Alternatively, the composition may be applied to prevent damage to the skin caused by environmental facts that sunscreen cannot protect against, such as, for example, damage caused by inflammation and infrared radiation.

The amount used is typically sufficient to obtain coverage of a desired area of the skin, such as the face, with a single application. The compositions may also be used over the course of a period of time, with the amount of the composition used including the amount used during repeated applications. For example, the compositions may be applied to a desired area of the skin on a daily basis, either once a day or several times per day, over the course of days, weeks, months or any time period desired by the user. The various compositions of the invention are typically considered to be light-weight, easily absorbed and layer cleanly under makeup or other substances applied to the skin without pilling or feeling heavy.

The topical skin care compositions of the various embodiments of the present invention may be formulated to be used on an "as needed" basis, or they may be formulated for application at specific times of the day, or multiple times during the time the user is awake. They may also be formulated for use on an every other day, weekly, monthly or other basis. The compositions may also be formulated for application by the fingers of the user, or they may be formulated for application by some application means, such as, for example, a soft pad or other applicator well known in the art. The compositions may also be used as part of a skin treatment regimen, and may also be used in conjunction with other skin creams and makeup.

In one embodiment, a user of a topical skin care composition in accordance with the present invention cleanses his/her skin and gently pats the skin dry. A thin, even layer of the skin care composition in accordance with the present invention is applied to the face, neck, or other portions of the body. The topical skin care composition is then gently massaged into the skin. This process may be performed every evening, for example.

While particular embodiments of the present invention have been described, it is understood that various different modifications within the scope and spirit of the invention are possible. The invention is limited only by the scope of the appended claims.

We claim:

1. A topical skin care composition comprising:
   (a) a meroterpene;
   (b) a complex including *bidens pilosa* extract, *elaeis guineesis* oil, *gossypium herbaceum* seed oil, and *linum usitatissimum* seed oil;
   (c) myristoyl tripeptide-31;
   (d) an oat avenanthramide extract;
   (e) an anti-inflammatory peptide;
   (f) a soy based active complex;
   (g) an argirilene-like peptide;
   (h) hyaluronic acid;
   (j) a water soluble enzyme;
   (k) an aloe barbadensis leaf extract;
   (l) oat β-glucan;
   (m) allantoin;
   (n) moisturizing saccharide complex;
   (o) a complex including rice extract, rosemary extract, sunflower extract and tocopherol;
   (p) an ascorbic acid source;
   (q) daikon radish oil; and
   (r) a cosmetically acceptable carrier.

2. The topical skin care composition of claim 1, wherein the aloe barbadensis extract is present in the amount of 0.01% to 0.50% by weight.

3. The topical skin care composition of claim 1, wherein the source of ascorbic acid is tetrahexydecyl ascorbate.

4. The topical skin care composition of claim 1, wherein the source of ascorbic acid is present in the amount of 0.01% to 10% by weight.

5. The topical skin care composition of claim 1, wherein the meteropene is bakuchiol.

6. The topical skin care composition of claim 1, wherein the daikon radish oil is present in the amount of 0.1% to 10.0% by weight.

7. The topical skin care composition of claim 1, wherein the moisturizing saccharide complex is an apple extract.

8. The topical skin care composition of claim 1, wherein the water soluble enzyme is derived from mushroom.

9. The topical skin care composition of claim 1, wherein the oat β-glucan is colloidal oatmeal.

10. The topical skin care composition of claim 1, wherein the argirilene-like peptide is palmitoyl hexapeptide-19.

11. The topical skin care composition of claim 1, wherein the sodium hyaluronic acid is combined with *chondrus crispus* extract and hydrolyzed *chrondrus crispus* extract.

12. The topical skin care composition of claim of claim 1, further comprising one or more emollient compounds.

13. The topical skin care composition of claim 1, further comprising an emulsifier.

14. The topical skin care composition of claim 1, wherein the anti-inflammatory peptide is capryloyl pentapeptide-26.

15. The topical skin care composition of claim 1, further comprising a pH modifier.

16. The topical skin care composition of claim 1, wherein the myristoyl tripeptide-31 is present in the amount of 0.1% to 4.0% by weight.

17. The topical skin care composition of claim 8, wherein the water soluble enzyme is a *mucor miehei* extract.

18. The topical skin care composition of claim 1, wherein the complex of *bidens pilosa* extract, *elaeis guineesis* oil, *gossypium herbaceum* seed oil, and *linum usitatissimum* seed oil is present in the amount of 0.1% to 3.0% by weight.

19. The topical skin care composition of claim 1, further comprising a viscosity modifier.

20. A method of treating the skin comprising applying to an outer surface of the skin the composition according to claim 1.

\* \* \* \* \*